(12) United States Patent
Petrick et al.

(10) Patent No.: US 6,989,538 B2
(45) Date of Patent: Jan. 24, 2006

(54) METHOD OF REDUCING RECOVERY TIME IN AN X-RAY DETECTOR

(75) Inventors: Scott William Petrick, Sussex, WI (US); Alan Dean Blomeyer, Milwaukee, WI (US); Richard Gordon Cronce, New Berlin, WI (US); Jeffrey Alan Kautzer, Pewaukee, WI (US)

(73) Assignee: General Electric Co., Schenectady, NY (US)

( * ) Notice: Subject to any disclaimer, the term of this patent is extended or adjusted under 35 U.S.C. 154(b) by 196 days.

(21) Appl. No.: 10/604,454

(22) Filed: Jul. 22, 2003

(65) Prior Publication Data

US 2005/0017187 A1    Jan. 27, 2005

(51) Int. Cl.
*G01J 1/44* (2006.01)
*G01T 1/24* (2006.01)
*H01L 25/00* (2006.01)
*H01L 27/00* (2006.01)
*H05G 1/64* (2006.01)

(52) U.S. Cl. .............................. 250/370.09; 250/370.11; 378/98.8

(58) Field of Classification Search ................. 250/363.01–363.09, 366, 370.06, 370.09, 250/370.11, 370.14, 252.1, 208.3; 378/98.8; 348/302, 306, 310, 313–314, 241
See application file for complete search history.

(56) References Cited

U.S. PATENT DOCUMENTS

| | | | |
|---|---|---|---|
| 5,920,070 A | 7/1999 | Petrick et al. | |
| 6,266,391 B1 * | 7/2001 | Albagli | 378/98.2 |
| 6,399,950 B1 * | 6/2002 | Kimura et al. | 250/370.09 |
| 6,696,687 B1 * | 2/2004 | Tomisaki et al. | 250/370.09 |
| 6,714,623 B2 * | 3/2004 | Sako et al. | 378/98.8 |

\* cited by examiner

*Primary Examiner*—David Porta
*Assistant Examiner*—Frederick F. Rosenberger
(74) *Attorney, Agent, or Firm*—Peter J. Vogel

(57) ABSTRACT

A method of maintaining an initial bias of an x-ray detector (12) includes setting the initial bias of the x-ray detector. Operating state of a readout circuit (30) is altered. A photodiode common contact voltage potential is adjusted by a data line drift amount to approximately maintain the initial bias. An x-ray imaging system (10) includes a detector (12) that has multiple pixels, multiple data lines (50), and a common contact (62) that is at a common contact voltage potential. The readout circuit (30) is electrically coupled to the data lines (50) and has a multiple power states. A controller (36) is electrically coupled to the readout circuit (30), detects a change in operating state of the readout circuit (30), and adjusts voltage potential of the common contact (62) in response to the change in operating state.

20 Claims, 7 Drawing Sheets

METHOD OF REDUCING RECOVERY TIME IN AN X-RAY DETECTOR

BACKGROUND OF INVENTION

The present invention relates generally to x-ray imaging systems, and more particularly, to a system and method of reducing recovery time of solid-state x-ray detectors within an x-ray system.

An x-ray system typically includes an x-ray beam source and an x-ray detector. An x-ray beam is directed by the x-ray source across a region of interest of a patient and is detected by the x-ray detector, which in turn generates projection data in response to the x-ray beam.

A solid-state x-ray detector commonly has an array of pixels composed of field effect transistors (FETs) that perform as switches and photodiodes, which detect light. The FETs and the photodiodes are constructed of amorphous silicon, over which cesium iodide (CsI) is deposited. The CsI absorbs x-rays, generated by the x-ray beam source, and converts them into light energy, which is then detected by the photodiodes.

The photodiode due to its construction performs as a capacitor and stores energy in the form of charge. Initialization of the detector occurs prior to an x-ray exposure during a technique that is commonly referred to as "scrubbing the detector" or simply "scrubbing". During scrubbing each photodiode is charged to a determined and initial voltage potential. The detector is then exposed to x-rays, which are absorbed by the CsI. Light that is emitted from the CsI is in proportion to flux of the x-rays and partially discharges the photodiodes. After conclusion of the exposure, voltage potential across the photodiodes is returned to the initial voltage potential. The amount of charge required to return the photodiodes to the initial voltage potential, is related to the x-ray dosage amount of a pixel integrated by a pixel coverage area for the length of an exposure.

The detector is read and scrubbed row by row, as controlled through active switching of the FETs. Reading is performed whenever an image produced by the detector contains valuable data, mainly images that contain exposure data or offset data. Since data acquired during scrubbing is not of interest it is discarded. Scrubbing is performed to maintain proper voltage bias across the photodiodes during idle periods or to perhaps reduce the effects of lag or incomplete charge restoration of the photodiodes.

There is a desire to minimize power dissipation within the x-ray system and the detector during the idle periods. One method of reducing power dissipation is to simply power off the detector between patients or between readings. However, since the detector is fabricated from amorphous silicon a substantial amount of time is required to stabilize the detector, causing a delay in use of the x-ray system.

Alternatively, part of the detector can be powered "OFF" to minimize stabilization time of the detector when full power is reapplied. In order to reduce this stabilization time, scan circuitry of the detector, which is used for scrubbing, is powered "ON" and is active. Readout circuitry of the detector, which is used to acquire data, can be powered OFF, because during idle time data is not acquired.

However, when powering OFF readout circuitry of an x-ray detector, voltage potential maintained across the photodiodes can change temporarily, potentially causing generation of a temporal error signal, which is added to valuable image or offset data until the maintained voltage potential stabilizes. This occurs since the cathode potential of the photodiodes is controlled by the readout circuitry via the data lines. When the readout circuitry is powered OFF, it no longer controls the potential of the data lines and therefore the potential of the cathodes of all the photodiodes, even when the potential of photodiode anodes remains constant. With the readout circuitry powered OFF, the data lines, and therefore the potentials of all the photodiode cathodes are free to drift toward the potential of the photodiode anodes, which is maintained during partial power OFF, and is the same potential for all of the photodiodes that form the detector.

When power is restored to the readout circuitry, the readout circuitry reestablishes an appropriate data line or photodiode cathode potential. Due to the parasitic impedance and capacitance of the data lines, the potential of the photodiode cathode requires a significant amount of time to stabilize. During this time, offset and image data is modified by the error signal.

Additionally, although data lines have associated readout channels that often maintain the data lines at a voltage potential level that is referred to as a virtual ground, the data lines can actually be slightly higher or lower than the virtual ground potential. This may be due to architecture, implementation, or simply process variation of a readout channel design.

It is therefore desirable to provide a method of reducing recovery time of an x-ray system detector so as to allow for reduced power dissipation. It is also desirable that the method minimizes generation and duration of error signals.

SUMMARY OF INVENTION

The present invention provides a system and method of reducing recovery time of solid-state x-ray detectors within an x-ray system. A method of maintaining an initial bias of an x-ray detector is provided. The method includes setting the initial bias of the x-ray detector. The operating state of a readout circuit is altered. A photodiode common contact voltage potential is adjusted by a data line drift amount to approximately maintain the initial bias.

An x-ray imaging system is also provided and includes a detector that has multiple pixels, multiple data lines, and a common contact that is at a common contact voltage potential. A readout circuit is electrically coupled to the data lines and has multiple power states. A controller is electrically coupled to the readout circuit, effects a change in operating state of the readout circuit, and adjusts voltage potential of the common contact in response to the change in operating state.

One of several advantages of the present invention is that it reduces recovery time of an x-ray system detector. In so doing the present invention maintains charge on detector photodiodes during idle periods.

Another advantage of the present invention is that it minimizes power dissipation during idle periods by allowing readout circuitry to be powered OFF and at the same time maintaining an approximately constant photodiode bias.

Furthermore, the present invention minimizes error signal generation due to inconsistent and varying voltage potential across photodiodes within the x-ray system detector during idle periods when the readout circuitry is powered OFF.

The present invention itself, together with attendant advantages, will be best understood by reference to the following detailed description, taken in conjunction with the accompanying FIGURES.

BRIEF DESCRIPTION OF DRAWINGS

For a more complete understanding of this invention reference should now be had to the embodiments illustrated in greater detail in the accompanying FIGURES and described below by way of examples of the invention wherein.

DETAILED DESCRIPTION

Figure 1:
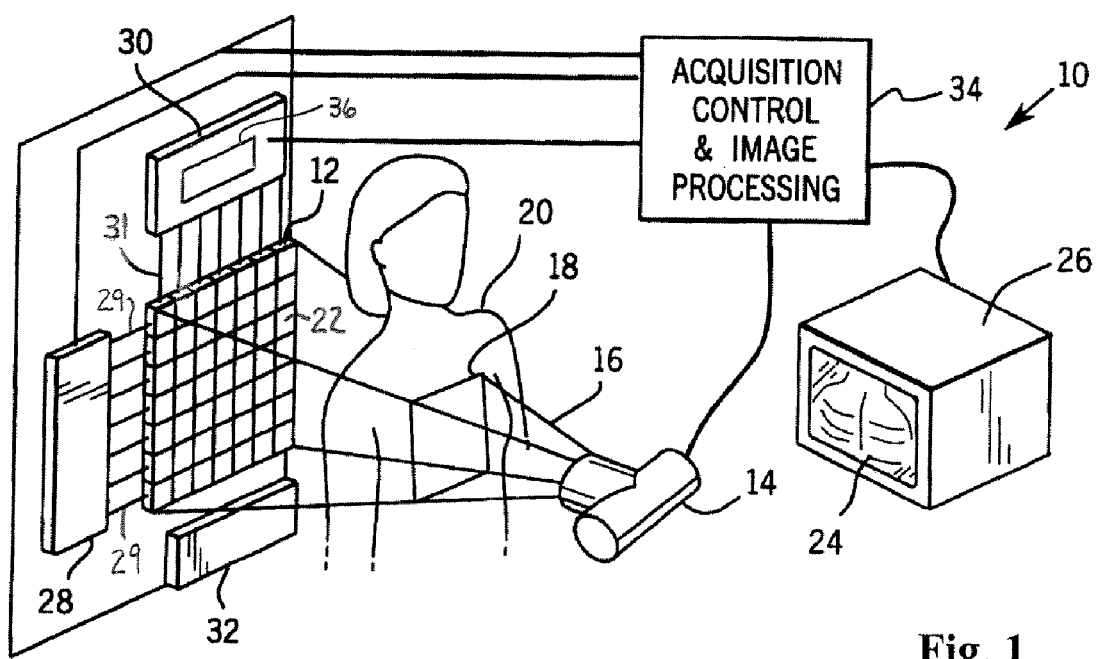
FIG. 1 is a perspective and block diagrammatic view of an x-ray imaging system utilizing a method of maintaining an initial bias status of an x-ray detector in accordance with an embodiment of the present invention.

In the following FIGURES, the same reference numerals will be used to refer to the same components. While the present invention is described with respect to a system and method of reducing recovery time of solid-state x-ray detectors within an x-ray system, the following system and method is capable of being adapted for various purposes and is not limited to the following applications: magnetic resonance imaging (MRI) systems, computed tomography (CT) systems, radiotherapy systems, x-ray imaging systems, ultrasound systems, nuclear imaging systems, magnetic resonance spectroscopy systems and other applications known in the art. The present invention may be applied to radiographic detectors, cardiographic detectors, or other detectors known in the art.

In the following description, various operating parameters and components are described for one constructed embodiment. These specific parameters and components are included as examples and are not meant to be limiting.

Referring now to FIG. 1, a perspective and block diagrammatic view of an x-ray imaging system 10 utilizing a method of maintaining an initial bias status of a detector array or x-ray detector 12 in accordance with an embodiment of the present invention is shown. The system 10 includes an x-ray source 14 that generates an x-ray beam 16, which is directed to pass through a region-of-interest 18 of a patient 20. The beam 16 is attenuated by internal structure of the patient 20 and is received by the detector 12.

The detector 12 is divided into multiple pixels 22. During operation, the pixels 22 are scanned by scanning circuitry 28, via scan lines 29, to generate exposure data. Readout circuitry 30 has multiple power states and receives and digitizes the exposure data through data lines 31. Each pixel 22 independently measures intensity of x-ray radiation received over a corresponding pixel exposed area or photodiode area (not shown) to generate the exposure data. A photodiode common bias or charge circuit 32 is electrically coupled to the detector and controls the anode voltage of the pixels 22, which is further described below.

An acquisition control and image processing circuit 34 is electrically coupled to the source 14, scanning circuitry 28, the readout circuitry 30, and the bias circuitry 32 and coordinates operation thereof. The acquisition processing circuit 34 reconstructs an image in response to the exposure data, which is displayed on the monitor 26.

A controller 36 is electrically coupled to the readout circuitry 30 and maintains the photodiode common bias voltage in response to variations in data line potential during transitions between various power states of the readout circuitry 30. Although, the controller 36 is shown as being part of the readout circuitry 30 it may be part of other circuitry, such as the photodiode common bias circuitry 32 or the image processing circuit 34.

The acquisition processing circuit 34 and the controller 36 are preferably microprocessor based such as a computer having a central processing unit, memory (RAM and/or ROM), and associated input and output buses. The acquisition circuit 34 and the controller 36 may simply be formed of logic state machines or of other logic devices known in the art. The acquisition processing circuit 34 and the controller 36 may be a portion of a central main control unit, an electronic control module, or may each be stand-alone controllers, as shown.

Figure 2:
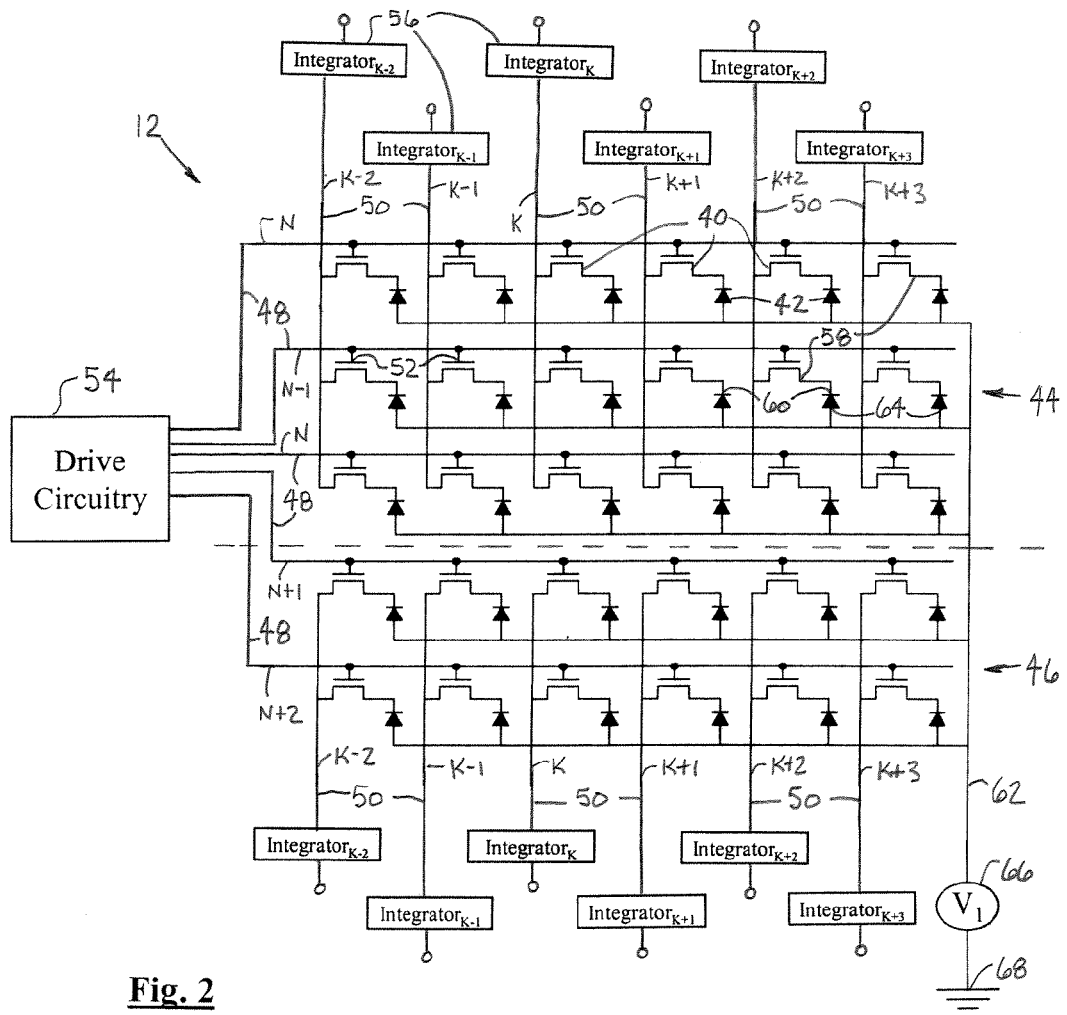
FIG. 2 is a schematic and block diagrammatic diagram of the x-ray detector in accordance with an embodiment of the present invention.

Referring now to FIG. 2, a schematic and block diagrammatic diagram of the x-ray detector 12 in accordance with an embodiment of the present invention is shown. As stated above the detector 12 includes the pixels 22, each of which having respective field effect transistors (FET) 40 and photodiodes 42. The detector 12 has a split design with a top half 44 and a bottom half 46. For example purposes, the pixels 22 are arranged rectangularly in rows and columns, of course other arrangements may be utilized. Each row designated by a scan line 48 and each column designated by a data line 50. The detector 12 has an approximately centered pixel designated by a scan line N and data line K. Although, a specified number of pixels 22 are shown, the detector 12 may have any number of pixels.

The scan lines are coupled between gate terminals 52 of the FETs 40 and drive circuitry 54. The data lines 50 are coupled between drain terminals of the FETs 40 and integrators 56. Source terminals 58 of the FETs are coupled to cathode 60 of the photodiodes 42. The scan lines 48 are used to activate the FETs 40 and simultaneously allow photodiodes 42 within a particular row to charge. The data lines 50 are used to charge the photodiodes 42, thereby collecting exposure or offset data.

Assuming the FET 40 to be an ideal switch, voltage potential across the photodiodes 42 between the data lines 50 and a photodiode common contact line 62 can be referred to as photodiode bias. The common contact 62 is coupled to anode 64 of the photodiodes 42 and is at a common contact voltage potential represented by source 66 having voltage $V_1$. Source 66 is coupled to ground 68.

In using the FETs 40, as known in the art, the number of electrical contacts to the detector 12 is reduced. Without use of the FETs 40, at least one contact for each pixel 22 is needed to activate the photodiodes 42, in effect limiting the number of pixels that may be manufactured in a single detector. The FETs 40 reduce number of required contacts to no more than the number of pixels 22 along a perimeter of the detector 12, or in other words the number of rows and columns.

Each pixel 22 on a scan line 48 is coupled to a different and separate data line 50. The data lines 50 are used by the readout circuitry 30 to restore charge to the photodiodes 50. As each scan line 48 is activated, all pixels 22 on that scan line 48 have respective photodiodes 42 that are simultaneously restored to an initial charge by the readout circuitry 30 over the data lines 50. Each data line 50 has an associated readout channel (not shown) from which the acquisition processing circuit 34 receives the exposed data.

The voltage across the photodiodes 42 is generally controlled by the bias circuit 32. The bias voltage to which the photodiodes 42 are charged is equal to difference between the voltage level of the common contact 62 and the voltage level of a respective photodiode data line 50. In order for the photodiodes 42 to store a capacitive charge, they are reversed biased, such that the photodiode anodes 64 are coupled to the common contact 62, which has a voltage potential that is more negative than that of the data lines 50.

On the other hand, potential of the common contact 62, which effects and is directly related to photodiode bias, is controlled by the controller 36. The controller 36 is electrically coupled to the data lines 50 and to the common contact 62. As voltage potential of the data lines 50 changes, the controller 36 compensates for these changes by adjusting voltage level of the common contact 62 by an averaged and approximately equal amount. This is explained in further detail below in the method of FIG. 6.

Figure 3:
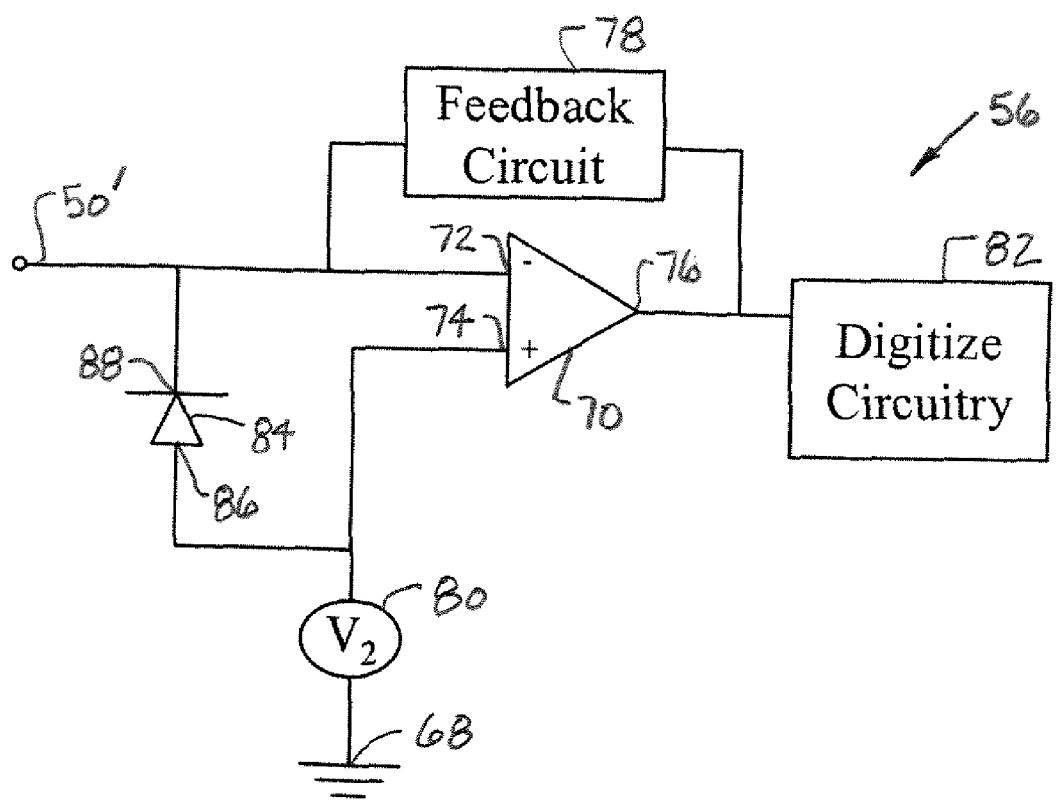
FIG. 3 is a schematic view of an integrator in accordance with an embodiment of the present invention.

Referring now to FIG. 3, a schematic view of the integrators 56 in accordance with an embodiment of the present invention is shown. Each data line 50 is electrically coupled to one of the integrators 56, which are included within the readout circuitry 30. Each integrator 56 includes an operational amplifier 70 having an inverting input 72, a non-inverting input 74 and an output 76. A feedback circuit 78 electrically couples the inverting input 72 to the output 76. The inverting input 72 is coupled to a data line 50'. The feedback circuit 78 may be capacitive or resistive in nature. The non-inverting input 74 is coupled to a second voltage source 80. The second voltage source 80 has a voltage potential $V_2$ and is coupled to ground 68. The non-inverting input 74 may be coupled to ground 68 or a source, such as source 80. Sources 66 and 80 are shown in FIGS. 2 and 3, to illustrate that the common contact 62 and the non-inverting input 74 are generally not at the same voltage level or at a true ground potential. The output 76 is coupled to digitize circuitry 82, which converts the exposed data in an analog format to a digital format for the acquisition processing circuit 34.

The integrator 56 due to its feedback circuit 78 maintains a constant potential on the inverting input 72. The constant potential is approximately equal to voltage potential at the non-inverting input 74, which as stated may be at a true ground potential or at some other potential such as the potential of source 80. When a scan line 48 is enabled and the FETs 40 are in an ON state or conducting state, connecting a selected number of the photodiodes 42 to the data lines 50, the amplifier 70 provides current necessary to charge the photodiodes 42 so that potential of the data lines 50 remains at the same potential as the non-inverting input 74.

A protection element 84, such as a diode is electrically coupled between the inverting input 72 and the source 80 and clamps the non-inverting input 74 during a power OFF state of the amplifier 70. The protection element 84 has an anode 86 and a cathode 88. The cathode 88 may be coupled to the inverting input 72 and the anode 86 may be coupled to the non-inverting input 74 or may be coupled to one of many supply pins (not shown) of amplifier 70. The protection element 84 may be a parasitic element, a design artifact of the amplifier 70, a protection diode, or some other protection element or elements known in the art. The protection element 84 may operate such that it is not normally conducting unless the amplifier 70 loses control of the corresponding data line, for example when power to the amplifier 70 is removed or perhaps under conditions of an electrostatic discharge on amplifier input pins, one of such being the non-inverting input 72.

Continuing with the example of power being removed from the amplifier 70, when a photodiode 42 is being scrubbed and a common potential is applied on the common contact 62 the data lines 50 tend to drift toward the common potential until the data lines drift 0.7 volts or one diode drop below ground potential, due to potential of source 80 being at approximately zero volts, or ground potential. The photodiodes 42 are scanned to provide instantaneous scanning ability when the readout circuitry 30 is powered ON, as known in the art. Once at a one diode drop below ground potential, the protection element 84 begins to conduct, due to leakage current of the photodiodes 42 during scrubbing or activation of the scan lines 48, and clamps the data lines 50 at approximately 0.7 volts. Of course, conduction of the protection element 84 is dependant upon relative voltage difference between the data lines 50 and the first source 66 or ground 68.

Amplifiers 70 in general consume a significant amount of power when in an ON state. The present invention provides low noise performance through use of amplifiers having a significant amount of power dissipation. The present invention by allowing the amplifiers 70 to be powered OFF between scans, conserves a significant portion of this power or energy loss and in so doing minimizes self-heating of the detector 12.

The integrator 56, as shown in FIG. 3, is an example of only one design and architectural possibility, other designs and architectures known in the art may be used to perform similarly.

Figure 4:
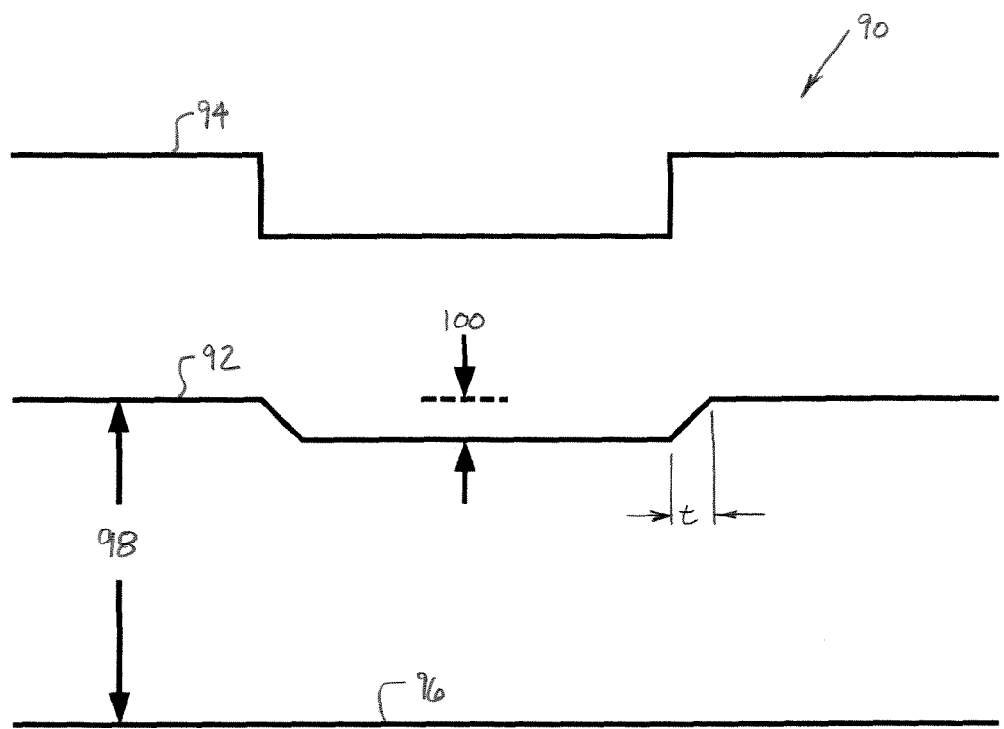
FIG. 4 is a traditional photodiode bias time line for a situation when amplifier power is deactivated.

Referring now to FIG. 4, a traditional photodiode bias time line 90 is shown for a situation when amplifier power is deactivated. The time line 90 illustrates change in data line potential 92 of a detector when amplifier power, represented by line 94, of a traditional x-ray imaging system is powered OFF, but photodiodes are scrubbed or scan lines are activated and a common potential 96 of a common contact of the photodiodes is maintained. Bias across the photodiodes is equal to difference between the data line potential and the common potential, designated by numerical designator 98.

Note that even though the data line potential 92 has a quick recovery time t after power is restored, since the traditional detector is fabricated from amorphous silicon it requires many scrub frames (not shown) before potential change in the data line is fully assimilated. During time t an apparent or error signal may be generated due to and directly related to change in the bias of the photodiode, represented by numerical designator 100. The error signal exists until the data line potential 92 is fully recovered. Image quality is adversely affected until the error signal decays to an acceptable level. Thus, depowering of the traditional amplifier is not normally preferred due to its associated negative results.

Figure 5:
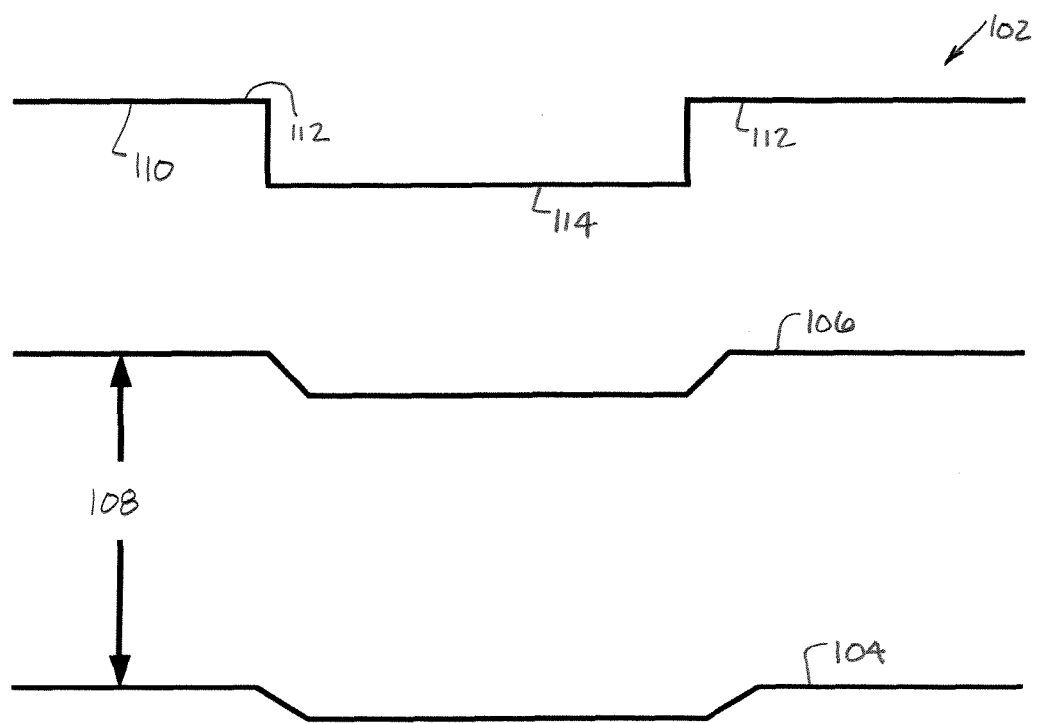
FIG. 5 is a photodiode bias time line in accordance with an embodiment of the present invention.

Referring now to FIG. 5, a photodiode bias time line 102 in accordance with an embodiment of the present invention is shown. The present invention adjusts potential of the common contact 62, represented by line 104, to follow change in data line potential when the amplifier 70 is in a powered OFF state. Data line potential is represented by line 106. State of the amplifier 70 is represented by line 110 and photodiode bias is represented by numerical designator 108.

The amplifier 70, for this embodiment has two states, an ON state 112 and an OFF state 114.

Although, potential adjustment of the common contact 62 may not exactly follow change in potential of the data lines 50 in time or magnitude, the difference between change in potential of the data lines 50 and change in potential of the common contact 62 is minimal. Thus, change in photodiode bias, which is equal to the difference between change in potential of the data lines 50 and change in potential of the common contact 62 is also minimal, resulting in a greatly reduced apparent signal or error signal. The error signal although being dependant upon sensitivity of the amplifier 70, clamping ability of the integrator 56, and other known system parameters, since it has a relatively smaller magnitude than that of a traditional error signal it has a substantially shorter decay time, or time to decay to an acceptable level before imaging can occur.

Before any adjustment in potential of the common contact 62 can be made when the readout circuitry 30 is powered off, a determination of the magnitude of that adjustment must be made and may be determined using methods known in the art. In determining magnitude of the adjustments, the readout circuitry 30 is used to measure the error signal immediately after power is restored to the readout circuitry 30 when no adjustment to the potential of the common contact 62 had been made and when the readout circuitry 30 was powered OFF, which allows the data line to "drift." This is advantageous for several reasons. First, the measurement is independent of architecture and no prior knowledge of the exact implementation of the readout circuitry 30 is required. Secondly, this technique lends itself to the implementation of dynamic adjustment of the potential of the common contact 62, which may compensate for other variables, such as change in temperature. Also, the above-described technique requires no additional measurement hardware. Other associated advantages will become apparent to those skilled in the art, in view of the following description.

The above-stated technique may be applied to each detector as part of a detector calibration. In current x-ray systems, a detector is calibrated for gain. As part of a calibration, bad pixels are also detected in order to be mapped out of diagnostic images. Calibrating each detector for data line drift when the readout circuitry is powered OFF may simply be another calibration routine, as depicted in FIG. 6.

Figure 6:
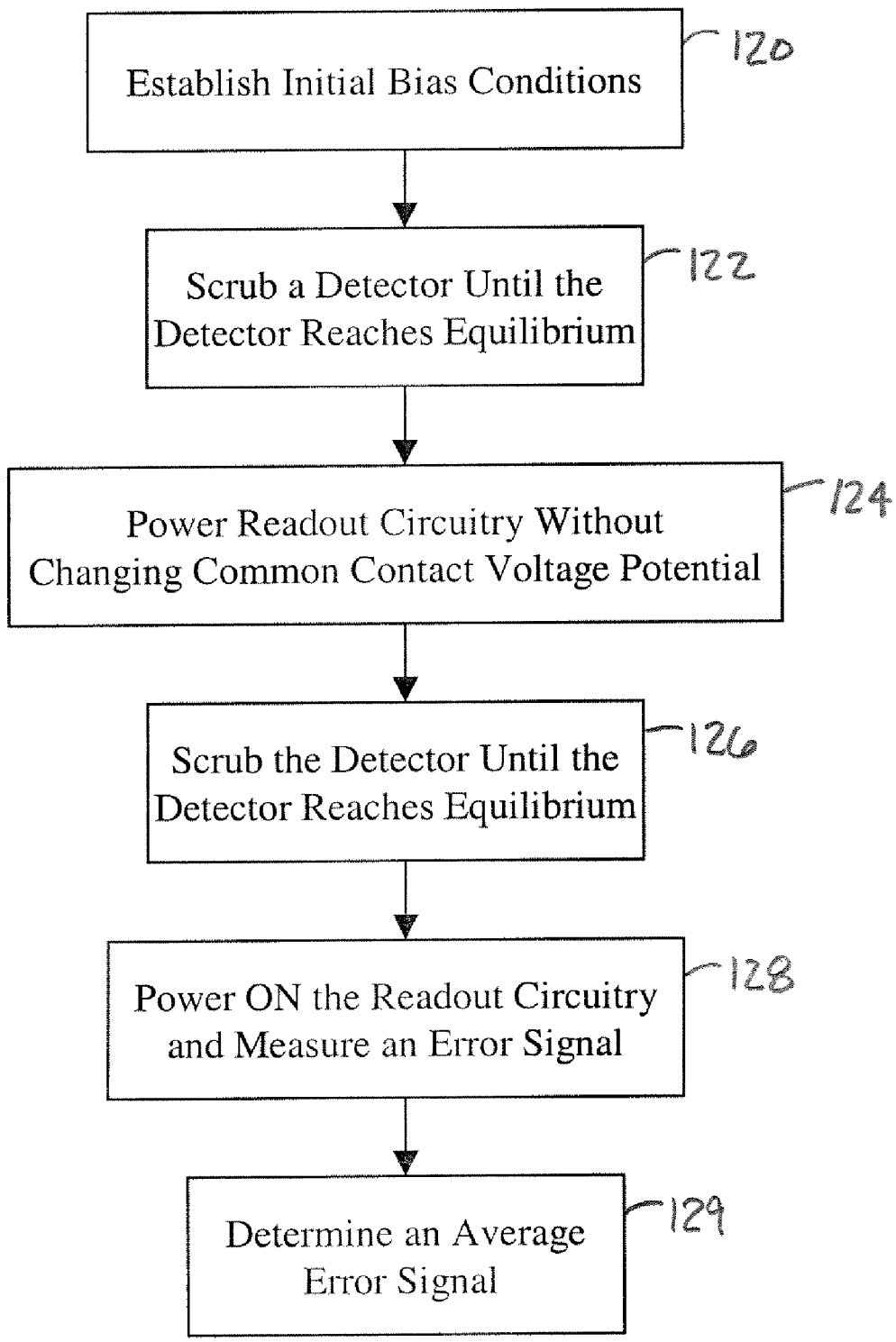
FIG. 6 is a logic flow diagram illustrating a method of determining data line drift within the x-ray imaging system of FIG. 1 and in accordance with an embodiment of the present invention.

Referring now to FIG. 6, a logic flow diagram illustrating a method of determining data line drift within the system 10 in accordance with an embodiment of the present invention is shown. In step 120 of FIG. 6, initial bias conditions are established by controller 36, such as potential of the common contact 62. The readout circuitry 30 is powered on by controller 36.

In step 122, the controller 36 scrubs the detector 12, thereby scanning it for a sufficient length of time so that the detector 12 reaches equilibrium.

In step 124, the controller 36 powers OFF the readout circuitry 30 without adjusting the potential of the common contact 62.

In step 126, the controller 36 continues to scrub the detector 12, again scanning until the detector 12 reaches equilibrium and the data lines 50 have drifted to the clamp voltages of the protection elements, such as element 84.

In step 128 controller 36 powers ON the readout circuitry 30 and uses it to measure the data line drift as represented by the error signal resulting from the restoration of the data line potential. Because no x-rays have been generated, the data line drift or error signal is a representation of how much to change potential of the common contact 62 in order to adjust for the change in the data line when the readout circuitry 30 is powered OFF. Since there is only one common contact and many data lines, the error signal from at least a significant or substantial subset of the data lines is averaged to determine adjustment of the common contact 62.

In step 129, the controller 36 determines an average error signal for all of the data lines 50. The controller 36 stores the common contact adjustment to minimize the resulting error signal when the power to the readout circuitry 30 is removed as part of normal operation (outside of calibration), as is described in further detail in the method of FIG. 7.

In an alternative embodiment, the calibration procedure of FIG. 6 is modified for production of many x-ray systems each of which having an x-ray detector, a common contact, and a controller, such as detector 12, common contact 62, and controller 36 or the like. A single calibration adjustment measurement may be determined for many detectors and for intended operating conditions during production or lab testing of the systems. An average measurement from the detectors is used rather than a single detector measurement, as described above. In this manner many detectors are characterized and a single adjustment in potential of the common contacts is determined and stored for use by the controllers. The same adjustment is used for every detector. This technique is not as flexible or accurate as performance of individual detector calibration, due to variation differences in the detectors. Also, since this technique or characterization may be done in a laboratory setting, independent of the controllers, individual sophistication level and costs of the controllers may be reduced over that of controller 36, due to calibration being performed for the controller before production rather than the controllers themselves performing calibration after production.

Figure 7:
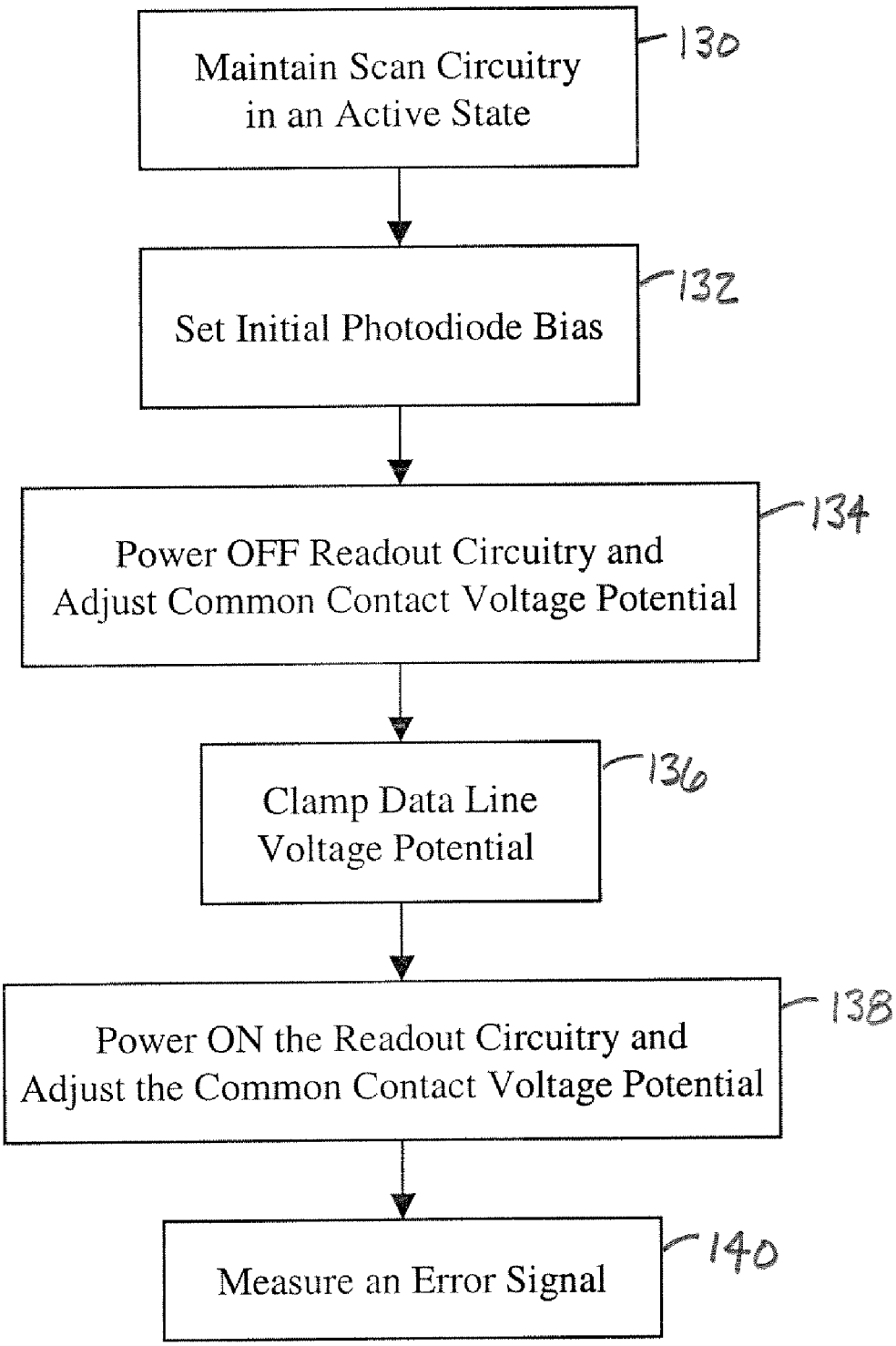
FIG. 7 is a logic flow diagram illustrating a method of maintaining an initial bias of an x-ray detector in accordance with an embodiment of the present invention.

Dynamic adjustment or calibration of data line drift may be performed at periodic time intervals, such as daily. For example, a calibration may be performed each day when the system 10 is readied for use before scanning of a first patient. The calibration may be initiated by the controller 36, in a manner that is transparent to the user, or may be initiated manually. The result of the calibration is used the first time that controller 36 powers OFF the readout circuitry 30. Potential of the common contact 62 is adjusted each time power of the readout circuitry 30 is cycled, as is depicted in the method of FIG. 7. In order to perform dynamic adjustment the sophistication level of the controller 36 is increased. Dynamic adjustment provides improved performance over either individual (static) calibration or characterization.

Referring now to FIG. 7, a logic flow diagram illustrating a method of maintaining an initial bias of the x-ray detector 12 in accordance with an embodiment of the present invention is shown. The method of maintaining change in photodiode bias is described with respect to an application when the system 10 is partially powered OFF, which refers to maintaining the scan circuitry 28 in an active state and powering OFF the readout circuitry 30. Also, the embodiment of FIG. 7 is described with respect to a situation when the readout circuitry 30 is powered OFF for any amount of time greater than the amount of time required for the data line to drift to voltage level of a clamping element, in this example the protection element 84. The present invention may be applied in various other situations where maintenance of photodiode bias is desired.

In step 130, the scan circuitry 28 is maintained in an active state. In step 132, the controller 36 sets an initial common contact 62 voltage potential that is used as a default or initial bias. This initial voltage potential for the common contact 62 represents a desired dynamic range of the detector 12, based on a nominal voltage potential of the data lines 50. The dynamic range is limited by both breakdown voltages of fabricated devices of the detector 12, which may be amorphous silicon type devices, as well as voltage dependent leakage characteristics of the photodiodes 42.

In step 134, the controller 36 due to system inactivity, a signal from an operator, or as part of a calibration powers OFF the readout circuitry 30, including amplifier 70, and adjusts voltage potential of the common contact 62 by an amount that the data line potential is expected to change when the readout circuitry 30 is powered OFF, as described above. In essence, the controller 36 powers OFF the readout circuitry 30 and adjusts the common contact potential when conditions for a power down of the readout circuitry 30 have been met.

In step 136, the protection element 84 clamps the data lines 50 at a predetermined voltage level. When, for example, a protection diode is used for the protection element 84, the protection diode clamps the data lines 50 to be at approximately 0.7 volts less than that of potential on non-inverting input 74 or potential of the source 80.

In step 138, the controller 36 powers ON the readout circuitry 30 and simultaneously adjusts voltage potential of the common contact 62 by approximately the same voltage potential magnitude as adjusted in step 134 but opposite in polarity to the adjustment made in step 134. Controller 36 performs this adjustment in response to an indication that the system 10 is set to generate diagnostic X-ray images of a patient or is set to be tested or recalibrated, other than calibration of change in potential of the data lines 50 when the readout circuitry 30 is powered OFF.

In step 140, for x-ray systems that interactively adjust change in potential of the common contact 62 each time that the readout circuitry 30 is cycled, such as system 10, the controller 36 may measure an apparent signal or error signal by cycling the readout circuitry 30. When the error signal is determined to be above a predetermined level, it is used to readjust potential of the common contact 62 when the next occurrence of the readout circuitry 30 is being powered OFF. Controller 36 determines an amount to dynamically adjust the potential of the common contact 62 and stores this amount in preparation for the next occurrence of the controller 36 powering OFF the readout circuitry 30.

In instances when the change in potential of the common contact 62 is not dynamically adjusted each time the readout circuitry 30 is powered OFF, step 140 is not performed. Accordingly, the potential of the common contact 62 is changed by the same magnitude each time that power of the readout circuitry 30 is cycled.

The above-described steps are meant to be an illustrative example; the steps may be performed synchronously, sequentially, simultaneously, or in a different order depending upon the application.

The present invention provides a method of maintaining a constant photodiode bias of an x-ray detector during various states of readout circuitry. In so doing, the present invention conserves on energy during periods when scanning is not being performed but yet maintenance of scanning circuitry is desired. The present invention reduces magnitude of generated error signals due to undesirable changes in data line potential and thus reducing recovery time.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

What is claimed is:

1. A method of maintaining an initial bias of an x-ray detector comprising:
   setting the initial bias of the x-ray detector;
   altering an operating state of a readout circuit; and
   adjusting a photodiode common contact voltage potential by a data line drift amount to approximately maintain the initial bias.

2. A method as in claim 1 further comprising maintaining scan circuitry in an active state.

3. A method as in claim 1 wherein adjusting a photodiode common contact voltage potential is performed by adjusting said photodiode common contact voltage potential by an amount approximately equal to an average change in a plurality of detector data line voltage potentials.

4. A method as in claim 1 further comprising:
   determining whether conditions for powering down said readout circuit have been satisfied;
   powering OFF said readout circuit and adjusting said common contact voltage potential in response to said determination; and
   clamping data line voltage potential.

5. A method as in claim 1 further comprising:
   powering ON said readout circuit; and
   adjusting said photodiode common contact voltage potential to an initial common contact voltage potential.

6. A method as in claim 1 wherein adjusting said photodiode common contact voltage is performed when a power state of said readout circuit is altered.

7. A method as in claim 1 further comprising:
   measuring an error signal; and
   readjusting said common contact voltage potential when said error signal is above a predetermined level.

8. A method as in claim 1 of determining data line drift within an x-ray system comprising:
   establishing initial bias conditions;
   scrubbing at least one detector until said at least one detector reaches equilibrium;
   altering operating state of at least one readout circuit without altering a common contact potential; and
   measuring data line drift.

9. A method as in claim 8 further comprising determining an average error signal for a plurality of data lines.

10. A method as in claim 8 wherein establishing initial bias conditions, scrubbing at least one detector, and altering operating state is performed via a controller.

11. An x-ray imaging system comprising:
    a detector having a plurality of pixels comprising;
    at least one data line; and
    a common contact at a common contact voltage potential;
    a readout circuit electrically coupled to said at least one data line and having a plurality of power states; and
    a controller electrically coupled to said readout circuit, detecting a change in bias between said at least one data line and said common contact, and adjusting active voltage potential of said common contact to an active non-zero voltage potential in response to said bias change.

12. A system as in claim 11 wherein said controller in adjusting voltage potential of said common contact maintains a scanning circuit in an active state.

13. A system as in claim 11 wherein said readout circuit comprises a plurality of integrators determining charge across a plurality of photodiodes.

14. A system as in claim 13 wherein said controller adjusts voltage potential of said common contact in response to said charge.

15. A system as in claim 11 wherein said controller enables x-ray image acquisition when voltage potential magnitude of an error signal is below a predetermined level.

16. An x-ray imaging system comprising:
   a detector having a plurality of pixels comprising;
   at least one data line; and
   a common contact at a common contact voltage potential;
   a readout circuit electrically coupled to said at least one data line and having a plurality of power states; and
   a controller electrically coupled to said readout circuit, detecting a change in operating state of said readout circuit, and adjusting voltage potential of said common contact in response to said change in operating state;
   wherein said controller adjusts voltage potential of said common contact in response to change in power state of said readout circuit.

17. An x-ray imaging system comprising:
   a detector having a plurality of pixels comprising;
   at least one data line; and
   a common contact at a common contact voltage potential;
   a readout circuit electrically coupled to said at least one data line and having a plurality of power states; and
   a controller electrically coupled to said readout circuit, detecting a change in operating state of said readout circuit, and adjusting voltage potential of said common contact in response to said change in operating state;
   wherein said readout circuit comprises:
      at least one integrator electrically coupled to said plurality of pixels; and
      a protection element electrically coupled to said integrator and conducting when said integrator is in a powered OFF state.

18. A system as in claim 17 wherein said protection element clamps voltage potential of at least one data line.

19. A system as in claim 17 wherein said controller detects said change and adjusts common contact voltage potential in response to power state of said integrator.

20. An x-ray imaging system comprising:
   a detector having a plurality of pixels comprising;
   at least one data line; and
   a common contact at a common contact voltage potential;
   a readout circuit electrically coupled to said at least one data line and having a plurality of power states; and
   a controller electrically coupled to said readout circuit, detecting a change in operating state of said readout circuit, and adjusting voltage potential of said common contact in response to said change in operating state;
   wherein said controller continuously adjusts common contact voltage potential to maintain an initial detector bias.

* * * * *